(12) United States Patent
Greenberg (10) Patent No.: US 9,682,209 B2
(45) Date of Patent: Jun. 20, 2017

(54) PATIENT INTERFACE DEVICE HAVING MODULAR HEADGEAR AND MASK COMPONENTS

(75) Inventor: Joshua Mark Greenberg, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 659 days.

(21) Appl. No.: 13/981,423

(22) PCT Filed: Jan. 27, 2012

(86) PCT No.: PCT/IB2012/050382
§ 371 (c)(1),
(2), (4) Date: Jul. 24, 2013

(87) PCT Pub. No.: WO2012/104757
PCT Pub. Date: Aug. 9, 2012

(65) Prior Publication Data
US 2013/0306077 A1    Nov. 21, 2013

Related U.S. Application Data

(60) Provisional application No. 61/439,136, filed on Feb. 3, 2011.

(51) Int. Cl.
*A61M 16/00* (2006.01)
*A61M 16/06* (2006.01)
*A62B 7/00* (2006.01)

(52) U.S. Cl.
CPC ........ *A61M 16/0683* (2013.01); *A61M 16/06* (2013.01); *A61M 16/0633* (2014.02); *A61M 2209/06* (2013.01); *A62B 7/00* (2013.01)

(58) Field of Classification Search
CPC .............. A61M 16/0683; A61M 16/06; A61M 16/0633; A61M 2209/06; A61M 16/00;
(Continued)

(56) References Cited

U.S. PATENT DOCUMENTS 3,505,998 A * 4/1970 Brown ...................... A61D 7/04
128/207.11
6,478,025 B1   11/2002 Yort
(Continued)

FOREIGN PATENT DOCUMENTS

AU   WO 2010/135785 A1 * 12/2010 ........ A61M 16/0644
WO         WO0132250 A1    5/2001
(Continued)

*Primary Examiner* — Lynne Anderson
*Assistant Examiner* — Elliot S Ruddie
(74) *Attorney, Agent, or Firm* — Michael W. Haas (57) ABSTRACT

A patient interface device (8) is includes a support frame (14) structured to be fluidly coupled to a pressure generating device, a cushion (12) structured to engage a portion of the face of a patient, and a headgear component (16) structured to secure the patient interface device to the head of the patient. The headgear component has a central interface portion (22), at least one strap member (24A, 24B) extending from the central interface portion, and a frame member (32) provided within central interface portion. The frame member is removeably secured in between the cushion and the support frame and is structured to provide an airtight seal between the cushion and the support frame.

15 Claims, 10 Drawing Sheets (58) Field of Classification Search
CPC .......... A61M 16/0616; A61M 16/0057; A61M
16/0066; A61M 16/0611; A61M 16/0622;
A61M 16/0688; A61M 16/0694; A61M
16/0816; A61M 16/0875; A61M 16/20;
A61M 2016/0661; A41D 13/11; A61D
7/04
USPC ............ 128/200.24, 205.25, 206.21, 206.24,
128/206.27, 207.11
See application file for complete search history.

(56) References Cited

U.S. PATENT DOCUMENTS

| | | | |
|---|---|---|---|
| 2005/0011521 A1* | 1/2005 | Sprinkle | A61M 16/06 128/206.21 |
| 2008/0053450 A1 | 3/2008 | Van Kerkwyk | |
| 2008/0087287 A1* | 4/2008 | Ging | A61M 16/06 128/207.11 |
| 2008/0178875 A1 | 7/2008 | Henry | |
| 2009/0107508 A1 | 4/2009 | Barmbilla | |
| 2010/0319700 A1* | 12/2010 | Ng | A61M 16/06 128/206.28 |

FOREIGN PATENT DOCUMENTS

| | | |
|---|---|---|
| WO | WO03082406 A2 | 10/2003 |
| WO | WO2007022562 A1 | 3/2007 |
| WO | WO2009108995 A1 | 9/2009 |

* cited by examiner

PATIENT INTERFACE DEVICE HAVING MODULAR HEADGEAR AND MASK COMPONENTS

CROSS-REFERENCE TO RELATED APPLICATIONS

This patent application claims the priority benefit under 35 U.S.C. §371 of international patent application no. PCT/IB2012/050382, filed Jan. 27, 2012, which claims the priority benefit under 35 U.S.C. §119(e) of U.S. Provisional Application No. 61/439,136 filed on Feb. 3, 2011, the contents of which are herein incorporated by reference.

BACKGROUND OF THE INVENTION

1. Field of the Invention

The present invention relates to respiratory patient interface devices, and, in particular, to a patient interface device having modular headgear and mask components in which the headgear component is structured to be selectively provided and attached between the frame/faceplate and cushion of the mask component.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Adherence and compliance to therapy, such as CPAP or other pressure support therapies, is growing to be an industry-wide issue. Factors such as comfort, ease of use and/or the ability to personalize components can greatly affect a patient's adherence and compliance to therapy. Thus, easier to use, simplified designs for patient interface devices are becoming expectations for any product that seeks to compete.

SUMMARY OF THE INVENTION

In one embodiment, a patient interface device is provided that includes a support frame structured to be fluidly coupled to a pressure generating device, a cushion structured to engage a portion of the face of a patient, and a headgear component structured to secure the patient interface device to the head of the patient. The headgear component has a central interface portion, at least one strap member extending from the central interface portion, and a frame member provided within central interface portion. The frame member is removeably secured in between the cushion and the support frame and is structured to provide an airtight seal between the cushion and the support frame.

In another embodiment, a patient interface system for selectively creating a customizable patient interface device is provided. The system includes a support frame structured to be fluidly coupled to a pressure generating device, a cushion structured to engage a portion of the face of a patient, and a plurality of headgear components. Each of the headgear components has a central interface portion and a frame member provided within central interface portion. The frame member of each of the headgear components is structured to be removeably secured in between the cushion and the support frame and is structured to provide an airtight seal between the cushion and the support frame. Also, each of the headgear components includes a different configuration of at least one strap member extending from the central interface portion and as such is structured to secure the support frame and cushion to a head of the patient in a different manner.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
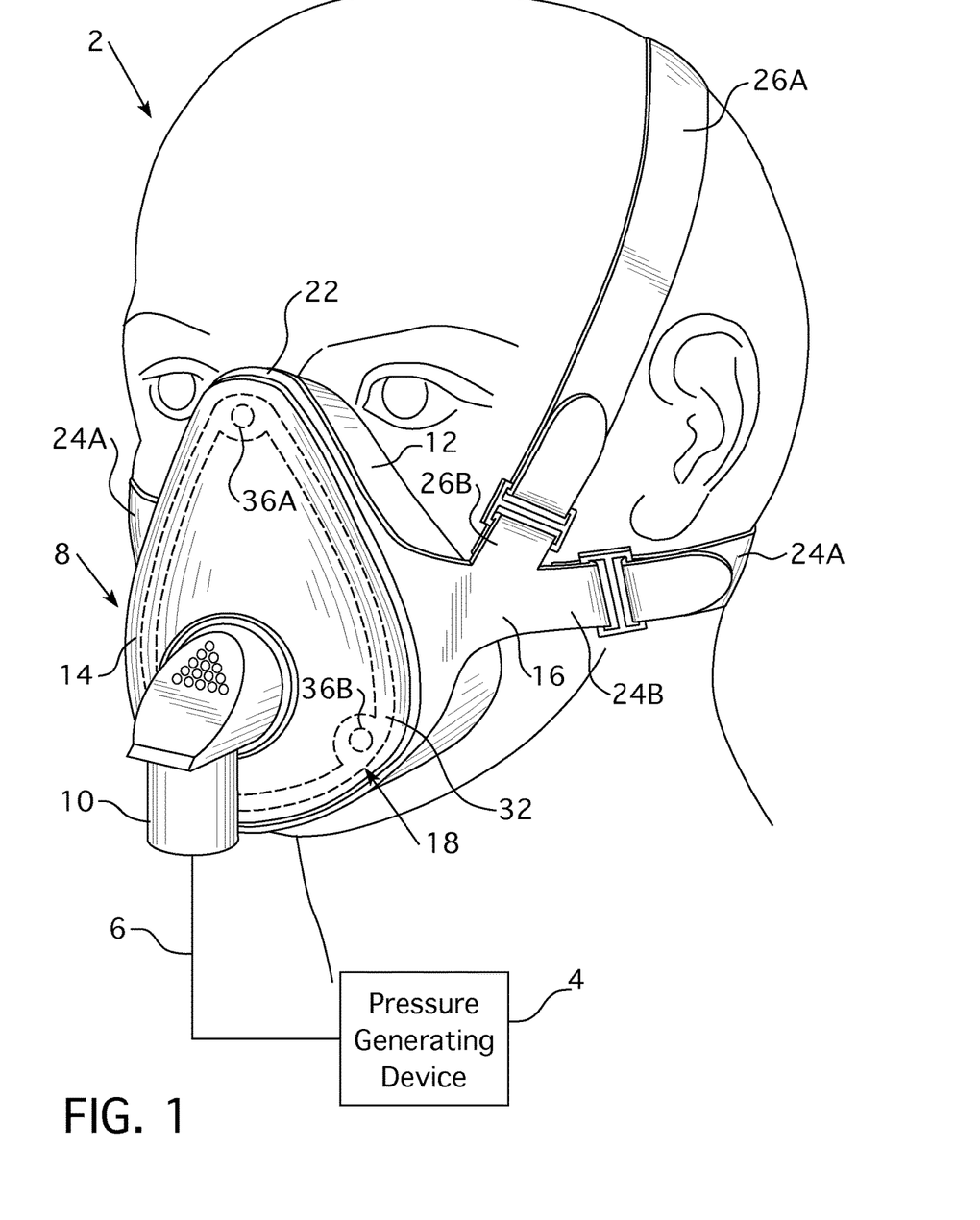
FIG. 1 is a schematic diagram of a system adapted to provide a regimen of respiratory therapy to a patient according to one exemplary embodiment of the present invention.

A system 2 adapted to provide a regimen of respiratory therapy to a patient according to one exemplary embodiment of the invention is generally shown in FIG. 1. System 2 includes a pressure generating device 4, a patient circuit 6, and a patient interface device 8 including a fluid coupling conduit 10 (e.g., an elbow conduit). Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Patient circuit 6 is structured to communicate the flow of breathing gas from pressure generating device 4 to patient interface device 8, and typically includes a gas delivery conduit or tube coupled to fluid coupling conduit 10.

In the illustrated embodiment, patient interface 8 is a nasaVoral mask that covers the nose and mouth of a patient. However, any type of patient interface device 8, such as a nasal cushion having nasal prongs that are received within the patient's nares, a nasal mask that covers the patient's nose, or a full face mask that covers the patient's face, which facilitates the delivery of the flow of breathing gas to, and the removal of a flow of exhalation gas from, the airway of such a patient may be used while remaining within the scope of the present invention.

In the embodiment shown in FIG. 1, patient interface 8 includes a cushion 12 configured to engage a portion of the patient's face, a rigid or semi-rigid frame or faceplate 14 configured to support cushion 12, and a headgear component 16 configured to secure patient interface device 8 to the patient's head. In the exemplary embodiment, cushion 12 is made of a soft, flexible material, such as, without limitation, silicone, an appropriately soft thermoplastic elastomer, a closed cell foam, gel, or any combination of such materials, and is configured to provide a flexible seal between the patient and patient interface device 8. As described in greater detail herein, cushion 12, faceplate 14 and headgear component 16 are coupled to one another in a configuration in which the headgear component is held and secured in between cushion 12 and faceplate 14 by way of a modular mating assembly 18 having portions that form parts of each of cushion 12, faceplate 14 and headgear component 16.

An opening provided in frame 14 to which fluid coupling conduit 10 is coupled allows the flow of breathing gas from pressure generating device 4 to be communicated to an interior space defined by cushion 12, and then, to the airway of a patient. The opening in frame 14 also allows the flow of exhalation gas (from the airway of such a patient) to be communicated to an exhaust port that may be provided, for example and without limitation, in fluid coupling conduit 10 or elsewhere on the patient interface device 8.

Figure 2:
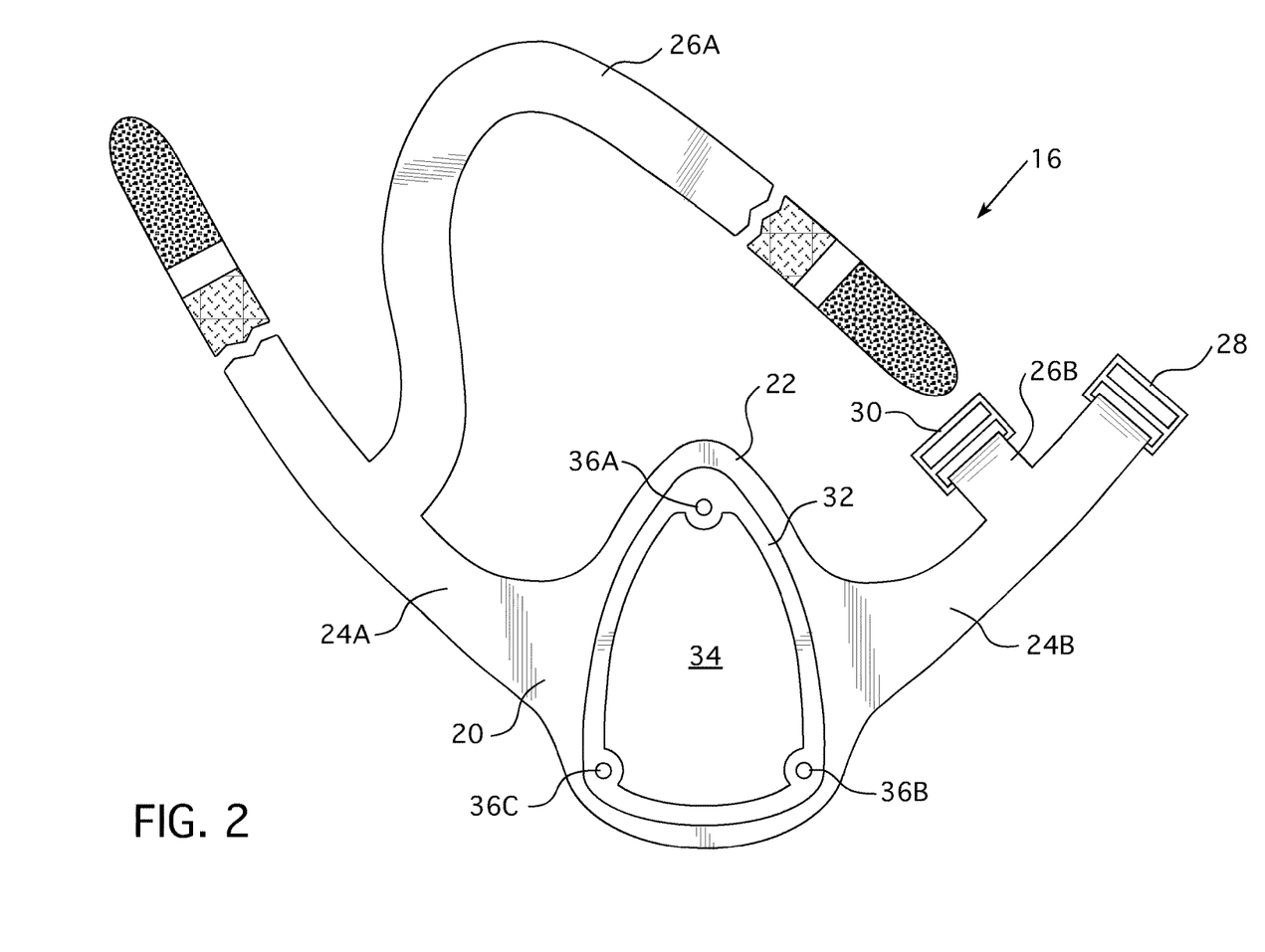
FIG. 2 is a top plan view of a headgear component according to one exemplary embodiment of the present invention forming a part of the system of FIG. 1.

FIG. 2 is a top plan view of headgear component 16 according to one exemplary embodiment of the present invention. Headgear component 16 includes a main body portion 20 made of a flexible material such as, without limitation, a fabric material like Lycra® (or another type of spandex material). As used herein, the term "fabric" shall mean a material consisting of a network of natural or artificial fibers made by, for example and without limitation, interlacing weaving, knitting, spreading, crocheting, or bonding the fibers to form the network. Main body portion 20 includes a central interface portion 22 and first and second lower strap members 24A, 24B that extend from either side of central interface portion 22. In addition, main body portion 20 also includes a first crown strap member 26A that extends upwardly from lower strap member 24A, and a second crown strap member 26B that extends upwardly from lower strap member 24B.

As seen in FIG. 1, headgear component 16 is configured to secure patient interface device 8 to the patient's head by way of first lower strap member 24A extending around the lower portion of the patient's head below the patient's ears and above the patient's neck and coupling to second lower strap member 24A, and by way of first crown strap member 26A extending over the crown of the patient' head and coupling to second crown strap member 26B. The fit and tension provided by each of coupled lower strap members 24A, 24B and coupled crown strap members 26A, 26B is selectively adjustable by way of a hook and loop fastening system, such as VELCRO®. In particular, the exterior of the end of each of first lower strap member 24A and first crown strap member 26A includes a hook fastener portion, and a corresponding loop fastener portion is provided on the exterior of each of first lower strap member 24A and first crown strap member 26A at a position spaced from the hook fastener portion.

In addition, as seen in FIG. 2, each of lower strap member 24B and crown strap member 26B includes a looped connecting element 28, 30. Thus, each of lower strap member 24A and crown strap member 26A may be threaded through the respective looped connecting element 28, 30 and then bent back on itself in order to adhere the hook fastener portion to the loop fastener portion at a selected location and couple to the components together. It will be understood that the illustrated hook and loop fastening arrangement is meant to be exemplary only, and that other selectively adjustable fastening arrangements are also possible within the scope of the present invention.

Headgear component 16 also includes a frame member 32 provided within central interface portion 22 (by, for example, a suitable adhesive or stitching). Frame member 32 is part of the modular mating assembly 18 described elsewhere herein. As seen in FIG. 2, frame member 32 defines an opening 34 and is attached within a corresponding opening provided within central interface portion 22. In the exemplary embodiment, frame member 32 is made of a thermoplastic polyurethane material, although other suitable materials may also be used, such as, without limitation although other suitable materials may also be used, such as, without limitation, another plastic material like polyvinyl chloride or polypropylene. In the exemplary embodiment, an important feature of frame member 32 is that it is deformable to an extent that it is able to provide an airtight seal between cushion 12 and faceplate 16 when patient interface device 8 is assembled as described elsewhere herein.

In the exemplary embodiment, the shape of frame member 32 generally corresponds to the shape of cushion 12 and faceplate 16. In the illustrated embodiment, each of frame member 32, cushion 12 and faceplate 16 have a generally triangular shape, although other shapes are possible within the scope of the present invention. As seen in FIG. 2, frame member 32 includes apertures 36A, 36B and 36C provided at each apex of frame member 32 which extend through frame member 32. The function of apertures 36A, 36B and 36C is described below in connection with the remaining portions of modular mating assembly 18.

Figure 3:
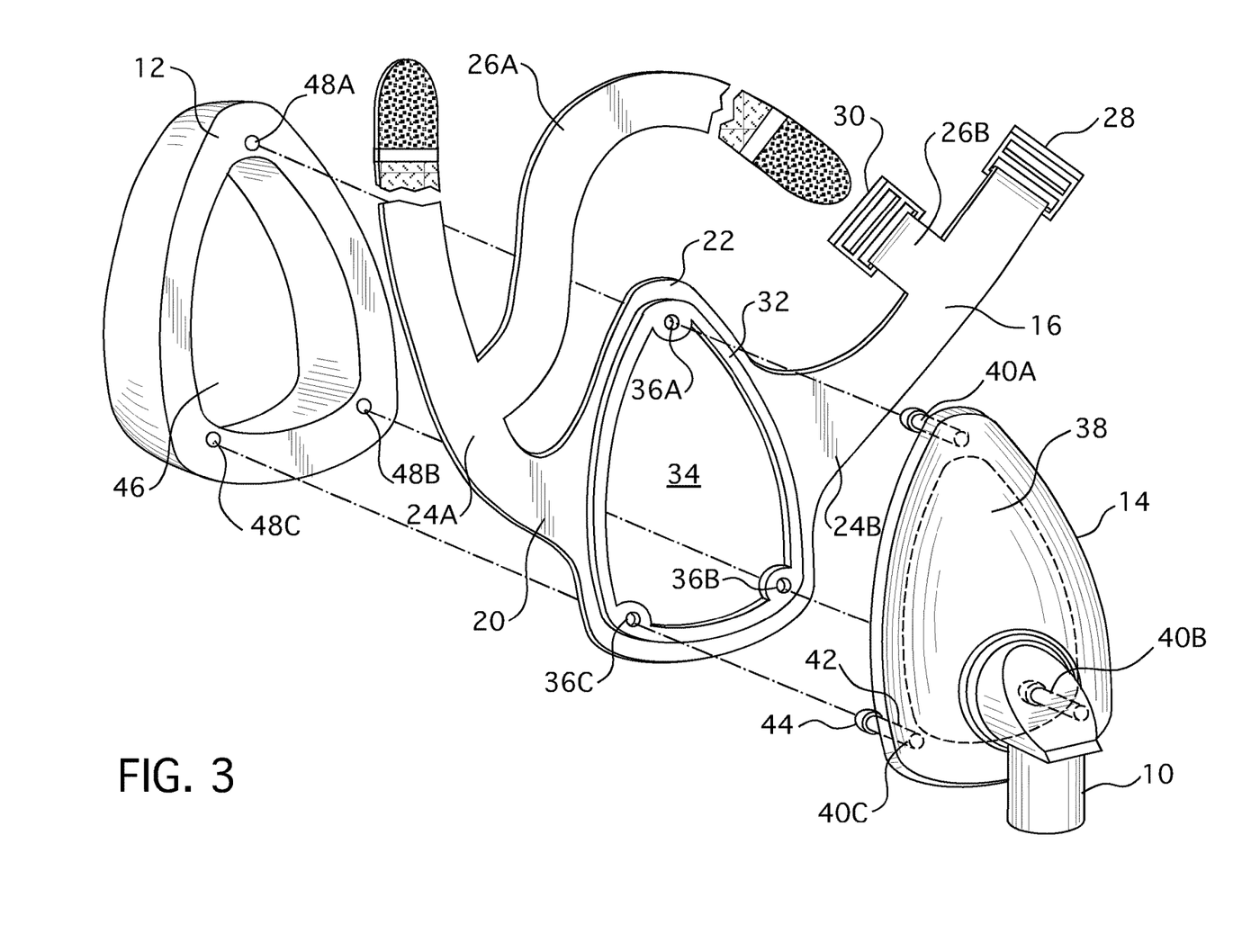
FIG. 3 is an exploded view of an exemplary embodiment of a patient interface device forming a part of the system of FIG. 1.

Referring to FIG. 3, which is an exploded view of the exemplary embodiment of patient interface device 8, faceplate 14 includes an opening 38 having a shape that corresponds to the shape of frame member 32. Faceplate 14 also includes pegs 40A, 40B, 40C provided around opening 38. Each peg 40A, 40B, 40C is a part of the modular mating assembly 18 that couples cushion 12, faceplate 14 and headgear component 16 to one another. In the illustrated embodiment, each peg 40A, 40B, 40C has a mushroom shape and includes a post portion 42 and an enlarged head portion 44. In addition, cushion 12 includes a main opening 46 having a shape that corresponds to the shape of frame member 32. Cushion 12 also includes holes 48A, 48B, 48C provided around opening 46 that extend into the exterior walls of cushion 12. Each hole 48A, 48B, 48C, like each peg 40A, 40B, 40C, is a part of the modular mating assembly 18 that couples cushion 12, faceplate 14 and headgear component 16 to one another.

To assemble patient interface device 8, headgear component 16, and in particular frame member 32 thereof, is positioned in between cushion 12 and faceplate 14 as shown in FIG. 3. In particular, cushion 12, faceplate 14 and headgear component 16 are arranged so that peg 40A is aligned with aperture 36A and hole 48A, peg 40B is aligned with aperture 36B and hole 48B, and peg 40C is aligned with aperture 36C and hole 48C. Headgear component 16 is then secured in between cushion 12 and faceplate 14 by inserting each peg 40A, 40b, 40C through the respective aperture 36A, 36B, 36C and hole 48A, 48b, 48C. Headgear component 16 may then be used to secure patient interface device 8 to the patient's head as described elsewhere herein for use. Other suitable connecting elements/mechanisms may also be used in place of the pegs and holes just described.

According to one particular embodiment, the assembly/mechanism for securing cushion 12, faceplate 14 and headgear component 16 to one another is modular in nature such that any headgear component that includes a frame member 32 can be used with cushion 12 and faceplate 14. Thus, a wide variety of headgear configurations, each having a frame member 32, can be offered for use with cushion 12 and faceplate 14 such that a patient can choose the particular headgear component that fits their particular needs or desires ant any one time, and can change the headgear component as those needs or desires change. To that end, FIGS. 4-7 show two alternative headgear components (labeled 16' and 16"), each having a frame member 32, that can used to provide such a modular patient interface device system. Also, any cushion and faceplate combination that has similarly positioned pegs 40A, 40B, 40C and holes 48A, 48b, 48C may be used with a headgear component that includes a frame member 32.

Figure 4:
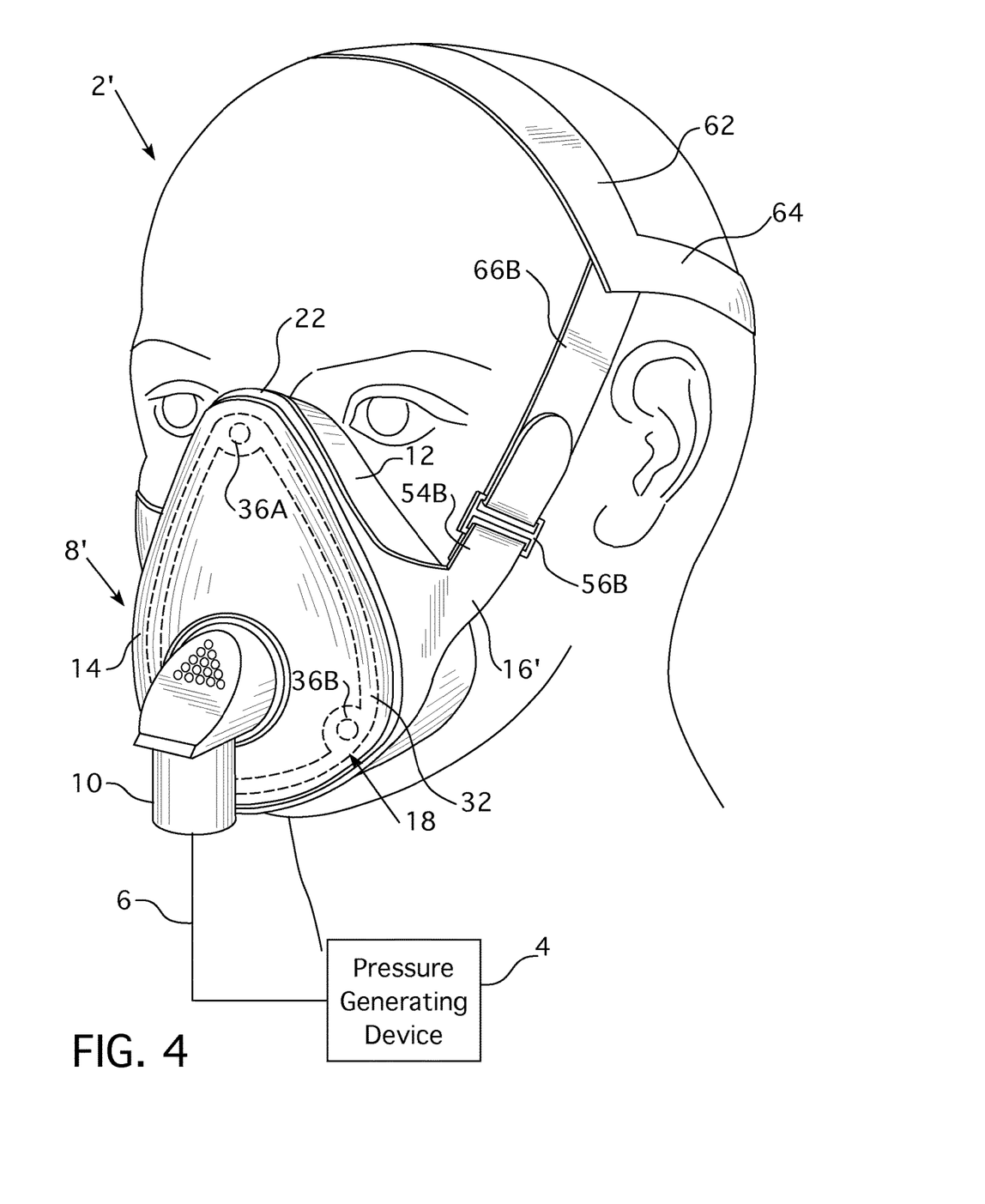
FIG. 4 is a schematic diagram of a system adapted to provide a regimen of respiratory therapy to a patient according to one alternative exemplary embodiment of the invention.

FIG. 4 is a schematic diagram of a system 2' adapted to provide a regimen of respiratory therapy to a patient according to one alternative exemplary embodiment of the invention. System 2' includes a number of the same components as system 2 shown in FIG. 1, and like components are labeled with like reference numerals. System 2' includes an alternative headgear component 16' structured to be provided and secured in between cushion 12 and faceplate 14.

Figure 5:
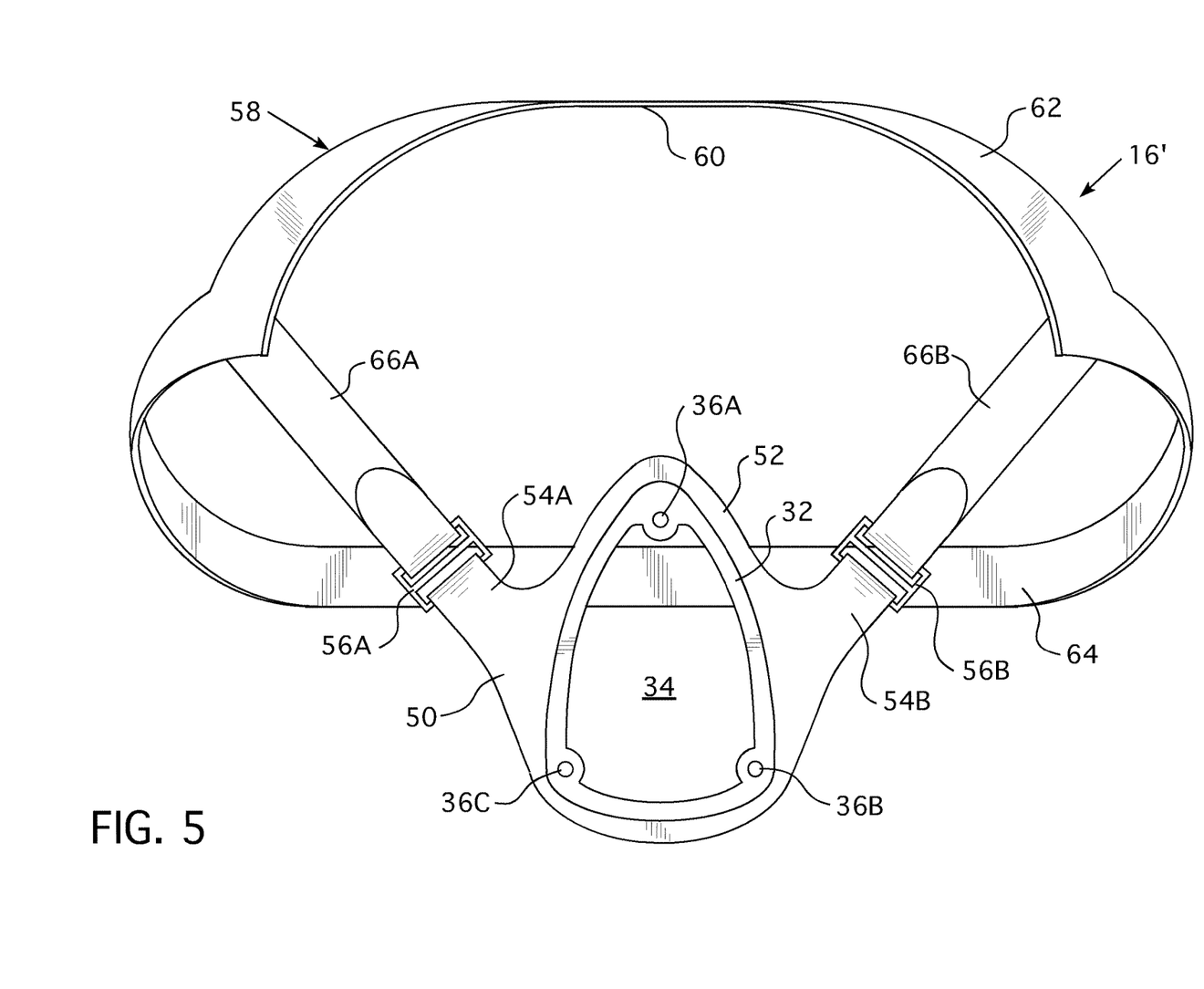
FIG. 5 is a top plan view of a headgear component according to an alternative exemplary embodiment of the present invention forming a part of the system of FIG. 4.

FIG. 5 is a top plan view of headgear component 16'. Headgear component 16 includes a main body portion 50 made of a flexible material such as, without limitation, a fabric material like Lycra® (or another type of spandex material). Main body portion 50 includes a central interface portion 52 and first and second strap members 54A, 54B that extend from either side of central interface portion 52. Each strap member 54A, 54B includes a looped connecting element 56A, 56B at the terminal end thereof. In addition, main body portion 50 also includes a crown member 58 comprising a central member 60 having a top strap 62, and a bottom strap 64, and first and second straps 66A, 66B that that extend from either side thereof.

As seen in FIG. 4, headgear component 16' is configured to secure patient interface device 8' to the patient's head by way of crown member 58 resting on top of the patient's head and strap members 66A, 66B extending toward cushion 12 and faceplate 14 above the patient's ears and coupling with looped connecting elements 56A, 56B. The fit and tension provided headgear component 16' is selectively adjustable by way of a hook and loop fastening system, such as VELCRO®, provided on strap members 66A, 66B as described in greater detail elsewhere herein. It will be understood that the illustrated hook and loop fastening arrangement is meant to be exemplary only, and that other selectively adjustable fastening arrangements are also possible within the scope of the present invention.

Headgear component 16' also includes a frame member 32 that is provided within central interface portion 52. Frame member 32 thus enables headgear component 16' to be secured in between cushion 12 and faceplate 14 by way of modular mating assembly 18 of which frame member 32 forms a part as described elsewhere herein.

Figure 6:
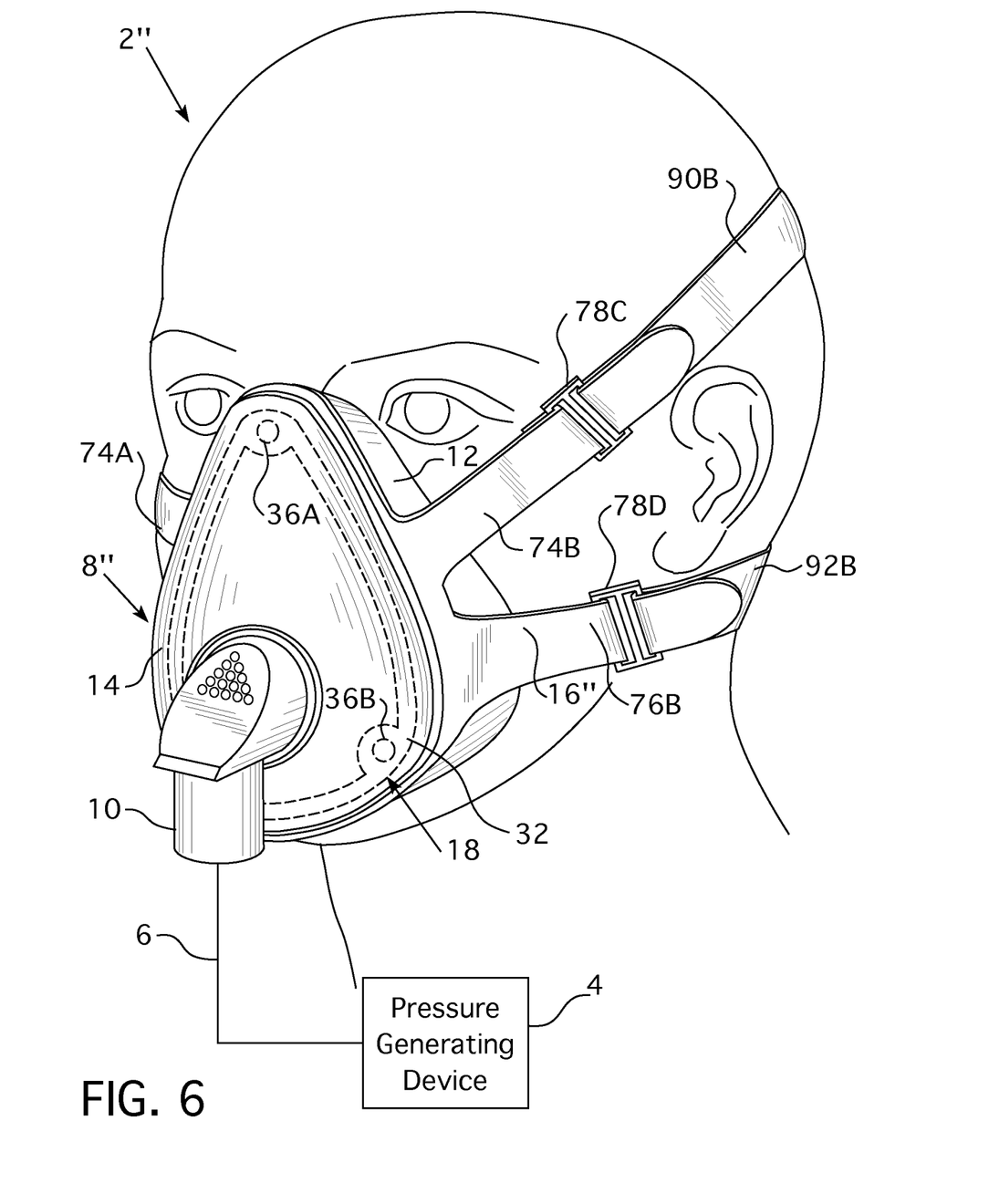
FIG. 6 is a schematic diagram of a system adapted to provide a regimen of respiratory therapy to a patient according to a further alternative exemplary embodiment of the invention.

FIG. 6 is a schematic diagram of a system 2" adapted to provide a regimen of respiratory therapy to a patient according to a further alternative exemplary embodiment of the invention. System 2" includes a number of the same components as system 2 shown in FIG. 1 and system 2' shown in FIG. 4, and like components are labeled with like reference numerals. System 2" includes an alternative headgear component 16" structured to be provided and secured in between cushion 12 and faceplate 14.

Figure 7:
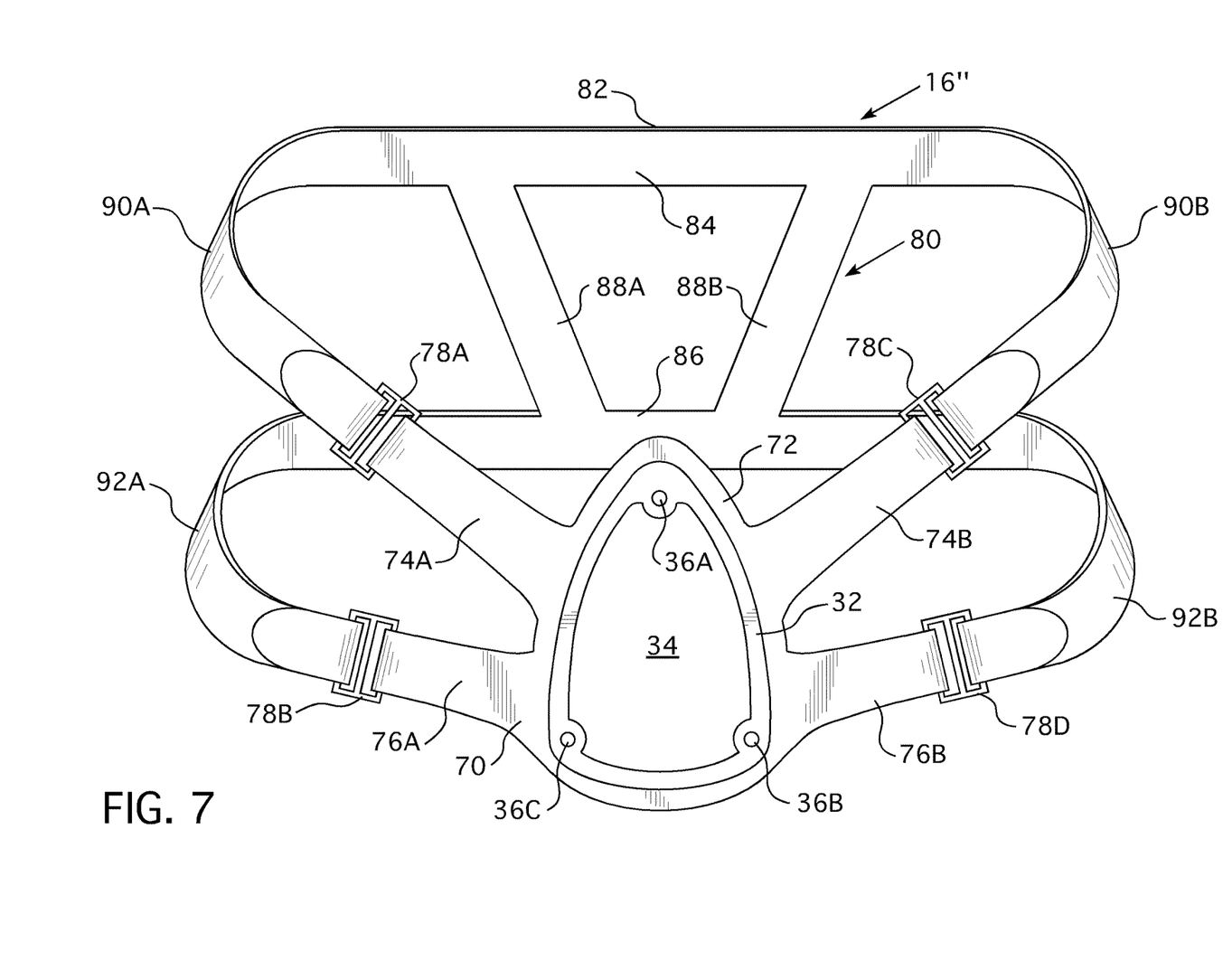
FIG. 7 is a top plan view of a headgear component according to an alternative exemplary embodiment of the present invention forming a part of the system of FIG. 6.

FIG. 7 is a top plan view of headgear component 16". Headgear component 16 includes a main body portion 70 made of a flexible material such as, without limitation, a fabric material like Lycra® (or another type of spandex material). Main body portion 70 includes a central interface portion 72 and top and bottom strap members 74A and 76A, respectively, that extend from a first side of central interface portion 72 and top and bottom strap members 74B and 76B, respectively, that extend from a second side of central interface portion 72. Each strap member 74A, 74B, 76A, 76B includes a looped connecting element 78A, 78B, 78C, 78D at the terminal end thereof. In addition, main body portion 70 also includes a back member 80 comprising a central member 82 having a top strap member 84, a bottom strap member 86, and cross strap members 88A, 88B provided between top strap member 84 and bottom strap member 86. Back member 80 further includes a top connecting strap 90A extending from a first side of top strap member 84, a top connecting strap 90B extending from a second side of top strap member 84, a bottom connecting strap 92A extending from a first side of bottom strap member 86, and a bottom connecting strap 92B extending from a second side of bottom strap member 86.

As seen in FIG. 6, headgear component 16" is configured to secure patient interface device 8" to the patient's head by way of central member 82 engaging the back of the patient's head and connecting strap members 90A, 90B, 92B, 92B extending toward cushion 12 and faceplate 14 above and below the patient's ears, respectively, and coupling with looped connecting elements 78A, 78B, 78C, 78D. The fit and tension provided headgear component 16" is selectively adjustable by way of a hook and loop fastening system, such as VELCRO®, provided on connecting strap members 90A, 90B, 92B, 92B as described in greater detail elsewhere herein. It will be understood that the illustrated hook and loop fastening arrangement is meant to be exemplary only, and that other selectively adjustable fastening arrangements are also possible within the scope of the present invention.

Headgear component 16" also includes a frame member 32 that is provided within central interface portion 72. Frame member 32 thus enables headgear component 16" to be secured in between cushion 12 and faceplate 14 by way of modular mating assembly 18 of which frame member 32 forms a part as described elsewhere herein.

Figure 8:
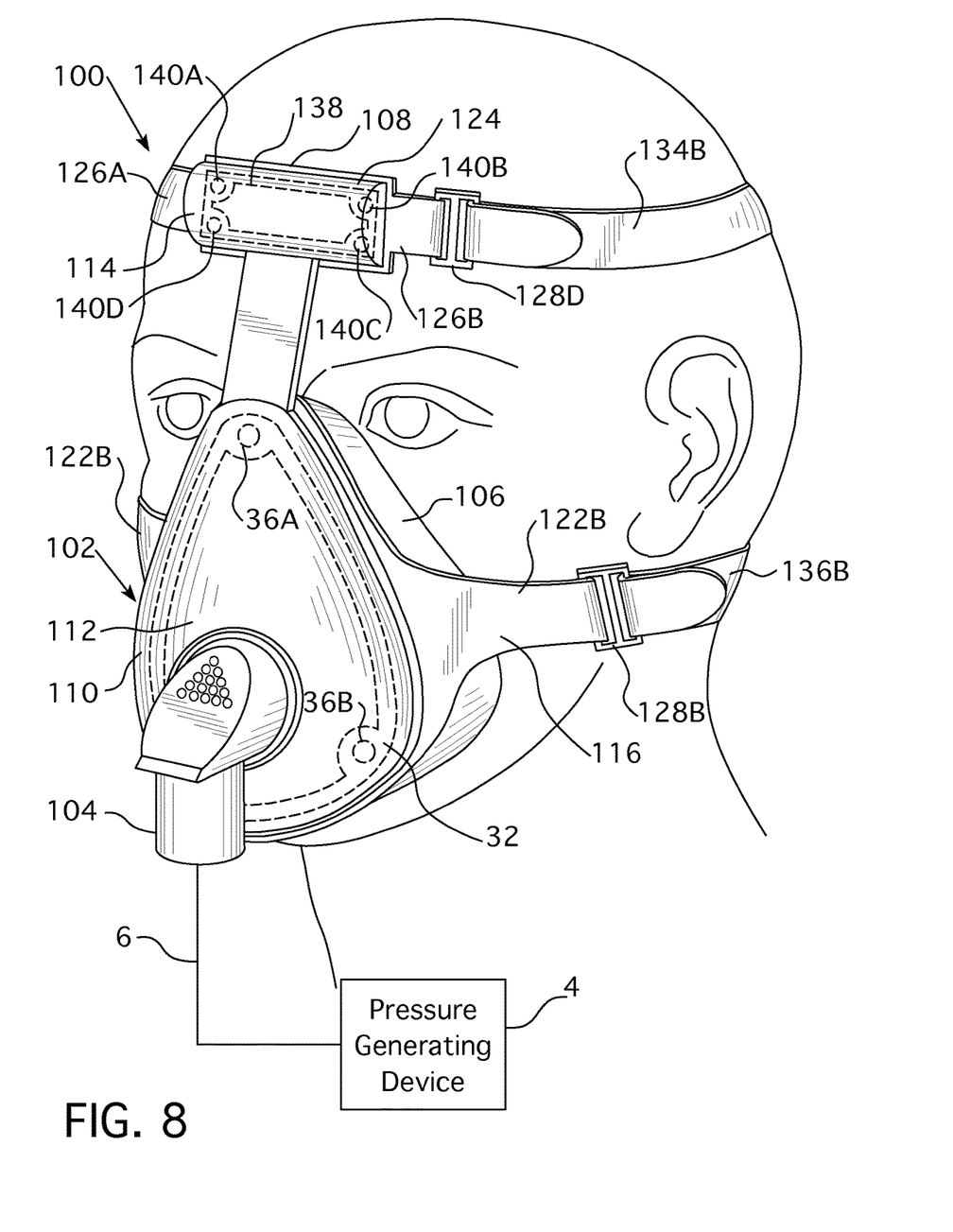
FIG. 8 is a schematic diagram of a system adapted to provide a regimen of respiratory therapy to a patient according to an alternative exemplary embodiment of the present invention.

A system 100 adapted to provide a regimen of respiratory therapy to a patient according to another exemplary embodiment of the invention is generally shown in FIG. 8. System 100 includes a pressure generating device 4 and a patient circuit 6 as described elsewhere herein. System 100 also includes an alternative patient interface device 102 including a fluid coupling conduit 104 (e.g., an elbow conduit). In the illustrated embodiment, patient interface 102 is a nasal/oral mask that covers the nose and mouth of a patient. However, other types of patient interface devices, such as a nasal mask that covers the patient's nose, which facilitate the delivery of the flow of breathing gas to, and the removal of a flow of exhalation gas from, the airway of such a patient may be used while remaining within the scope of the present invention.

Figure 9:
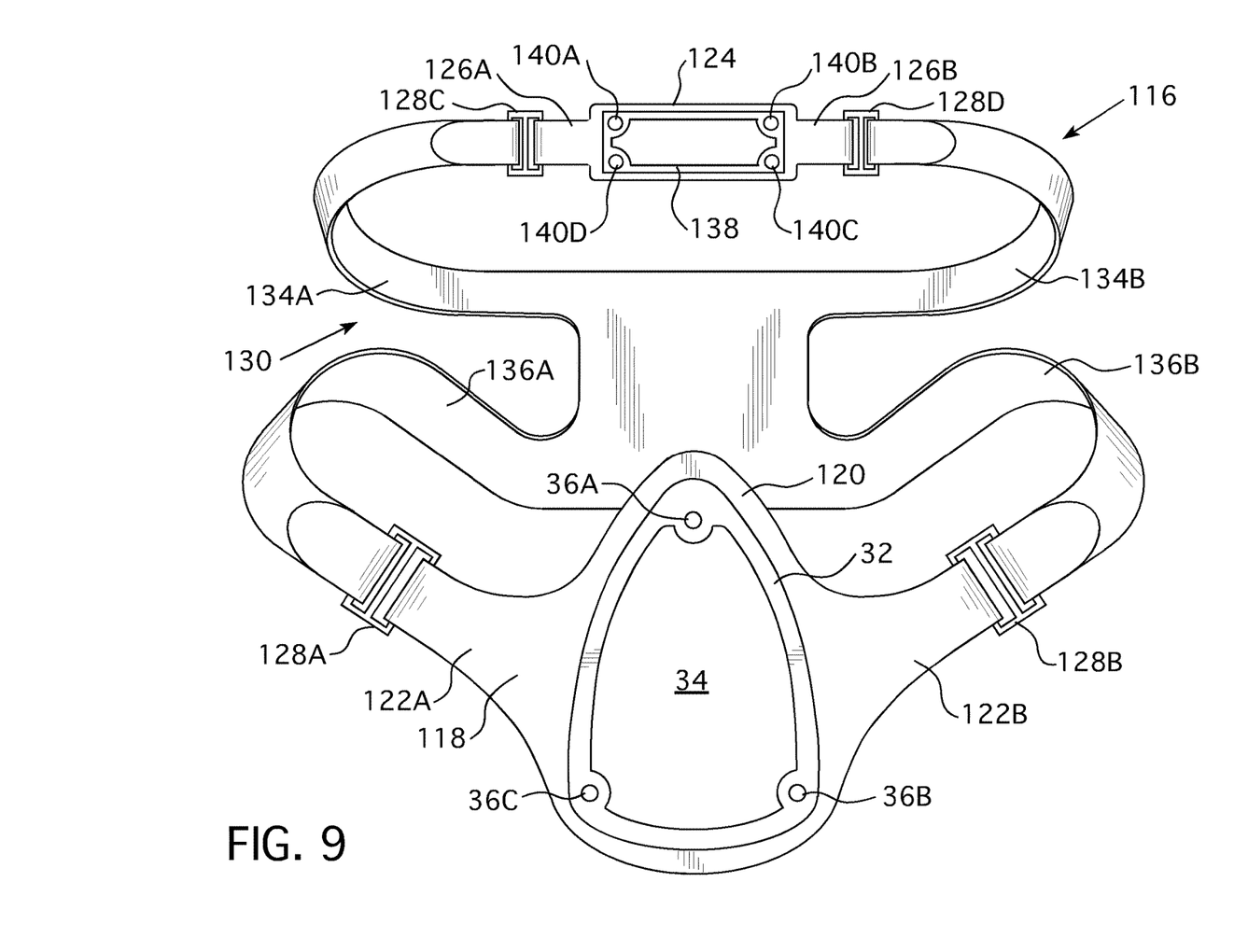
FIG. 9 is a top plan view of a headgear component according to one exemplary embodiment of the present invention forming a part of the system of FIG. 8.
Figure 10:
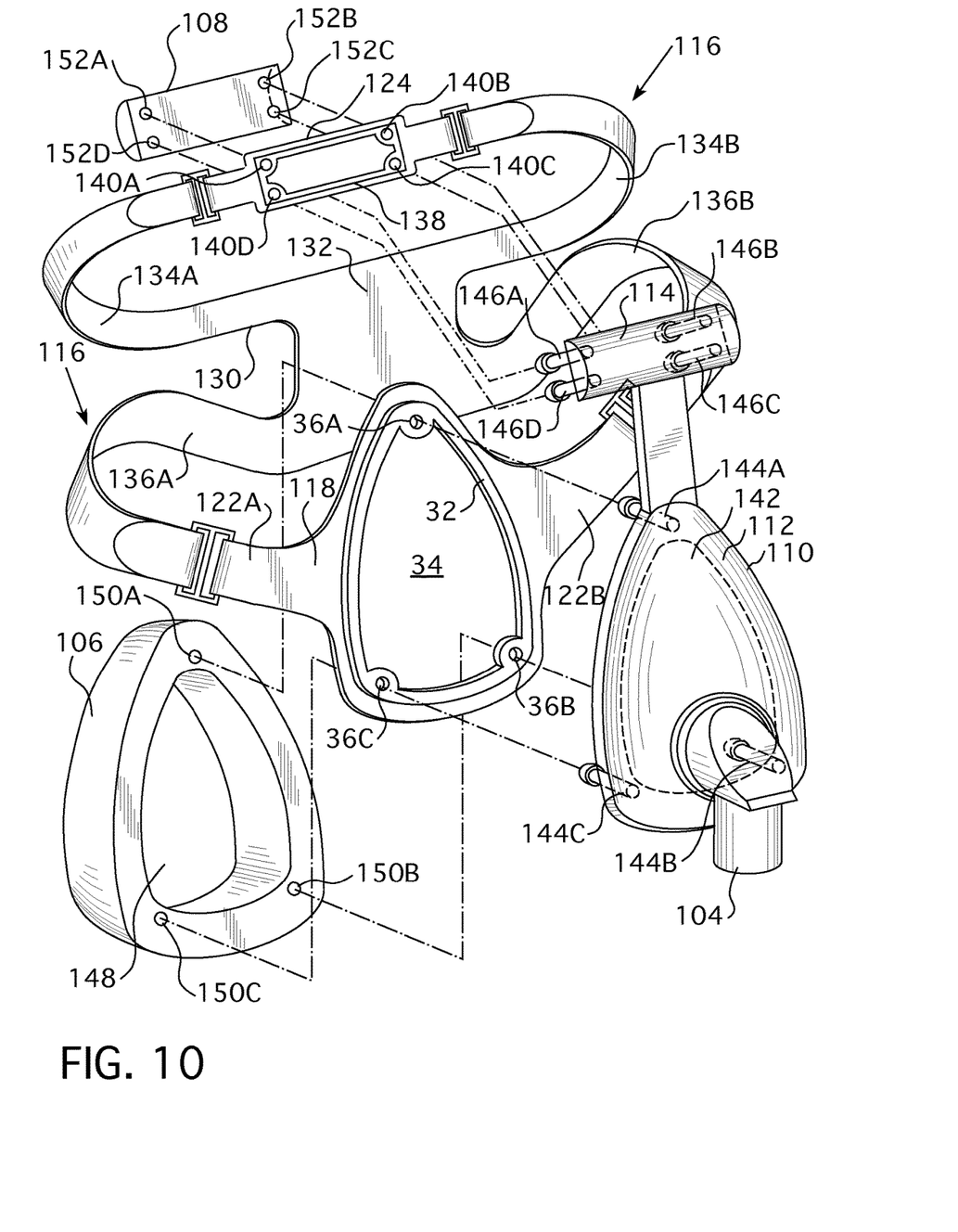
FIG. 10 is an exploded view of an exemplary embodiment of a patient interface device forming a part of the system of FIG. 8.

In the embodiment shown in FIGS. 8-10, patient interface 102 includes a cushion 106 configured to engage a portion of the patient's face, and a forehead cushion 108 configured to engage the patient's forehead. In the exemplary embodiment, cushion 106 and forehead cushion 108 are each made of a soft, flexible material, such as, without limitation, silicone, an appropriately soft thermoplastic elastomer, a closed cell foam, gel, or any combination of such materials. In addition, cushion 106 is configured to provide a flexible seal between the patient and patient interface device 102. Patient interface device 102 further includes a rigid or semi-rigid frame 110 having a faceplate portion 112 configured to support cushion 106 and a forehead support portion 114 configured to support forehead cushion 108. A headgear component 116 configured to secure patient interface device 102 to the patient's head is also provided. As described in greater detail herein, cushion 106, forehead cushion 108, frame 110 and headgear component 116 are coupled to one another in a configuration wherein headgear component 116 is held and secured in between cushion 106 and faceplate portion 112 and in between forehead cushion 108 and forehead support portion 114 by way of a modular mating assembly having portions that form parts of each of cushion 106, forehead cushion 108, frame 110 and headgear component 116.

An opening provided in faceplate portion 112 to which fluid coupling conduit 104 is coupled allows the flow of breathing gas from pressure generating device 4 to be communicated to an interior space defined by cushion 108, and then, to the airway of a patient. The opening in faceplate portion 112 also allows the flow of exhalation gas (from the airway of such a patient) to be communicated to an exhaust port that may be provided, for example and without limitation, in fluid coupling conduit 104 or elsewhere on the patient interface device 102.

FIG. 9 is a top plan view of headgear component 116 according to one exemplary embodiment of the present invention. Headgear component 116 includes a main body portion 118 made of a flexible material such as, without limitation a fabric material like Lycra® (or another type of spandex material). Main body portion 118 includes a central interface portion 120 and first and second lower strap members 122A, 122B that extend from either side of central interface portion 120. Main body portion 118 also includes a forehead portion 124 and first and second upper strap members 126A, 126B that extend from either side of forehead portion 124. Each strap member 122A, 122B, 124A, 124B includes a looped connecting element 128A, 128B, 128C, 128D at the terminal end thereof. In addition, main body portion 118 also includes a back member 130 comprising a central member 132 having a top connecting strap 134A and a bottom connecting strap 136A extending from a first side thereof and a top connecting strap 134B and a bottom connecting strap 136B extending from a second side thereof.

As seen in FIG. 8, headgear component 116 is configured to secure patient interface device 102 to the patient's head by way of central member 132 engaging the back of the patient's head and connecting strap members 134A, 134B, 136B, 136B extending toward frame 110 above and below the patient's ears, respectively, and coupling with looped connecting elements 128A, 128B, 128C, 128D. The fit and tension provided headgear component 116 is selectively adjustable by way of a hook and loop fastening system, such as VELCRO®, provided on connecting strap members 134A, 134B, 136B, 136B as described in greater detail elsewhere herein. It will be understood that the illustrated hook and loop fastening arrangement is meant to be exemplary only, and that other selectively adjustable fastening arrangements are also possible within the scope of the present invention.

Headgear component 116 also includes a frame member 32 provided within central interface portion 120, and a forehead frame member 138 provided within forehead portion 124. Frame member 32 and forehead frame member 138 are each part of the modular mating assembly described elsewhere herein. Frame member 32 is described in detail elsewhere herein in connection with the embodiments of FIGS. 1-7. In addition, as seen in FIG. 9, forehead frame member 138 is attached within an opening provided within forehead portion 124. In the exemplary embodiment, forehead frame member 138, like frame member 32, is made of a thermoplastic polyurethane material, although other suitable materials may also be used, such as, without limitation, another plastic material like polyvinyl chloride or polypropylene. In the exemplary embodiment, the shape of forehead frame member 138 generally corresponds to the shape of forehead cushion 108 (in the illustrated, non-limiting embodiment, a rectangular shape is employed).

As seen in FIG. 9, frame member 32 includes apertures 36A, 36B and 36C provided at each apex of frame member 32 which extend through frame member 32, and forehead frame member 138 includes apertures 140A, 140B, 140C and 140D provided at each corner of forehead frame member 138 which extend through forehead frame member 138. The function of apertures 36A, 36B and 36C and apertures 140A, 140B, 140C and 140D is described below in connection with the remaining portions of modular mating assembly 118.

Referring to FIG. 10, which is an exploded view of the exemplary embodiment of patient interface device 102, faceplate portion 112 includes an opening 142 having a shape that corresponds to the shape of frame member 32. Faceplate portion 112 also includes pegs 144A, 144B, 144C provided around opening 142. Similarly, forehead support portion 114 includes pegs 146A, 146B, 146C, 146D provided around the outer periphery thereof. Each peg 144A, 144B, 144C, 146A, 146B, 146C, 146D is a part of the modular mating assembly that couples cushion 106, forehead cushion 108, frame 110 and headgear component 116 to one another.

In the illustrated embodiment, each peg 144A, 144B, 144C, 146A, 146B, 146C, 146D has a mushroom shape and includes a post portion and an enlarged head portion. In addition, cushion 106 includes a main opening 148 having a shape that corresponds to the shape of frame member 32. Cushion 106 also includes holes 150A, 150B, 150C provided around opening 148 that extend into the exterior walls of cushion 106, and forehead cushion 108 includes holes 152A, 152B, 152C, 152D provided around the outer periphery thereof. Each hole 150A, 150B, 150C, 152A, 152B, 152C, 152D is also a part of the modular mating assembly 118 that couples cushion 106, forehead cushion 108, frame 110 and headgear component 116 to one another.

To assemble patient interface device 102, frame member 32 is positioned in between cushion 106 and faceplate portion 112 and forehead frame member 138 is positioned in between forehead cushion 108 and forehead support portion 114 as shown in FIG. 10. In particular, cushion 106, faceplate portion 112 and headgear component 116 are arranged so that each peg 144A, 144B, 144C is aligned with a respective aperture 36A, 36B, 36C and hole 150A, 150B, 150C, and forehead cushion 108 forehead support portion 114, and headgear component 116 are arranged so that each peg 146A, 146B, 146C, 146D is aligned with a respective aperture 140A, 140B, 140C and 140D and hole 152A, 152B, 152C, 152D. Headgear component 116 is then secured in between cushion 106 and faceplate portion 112 and in between forehead cushion 108 and forehead support portion 114 by inserting each peg through the respective aperture and hole. Headgear component 116 may then be used to secure patient interface device 102 to the patient's head as described elsewhere herein for use.

According to one particular embodiment, the assembly/mechanism for securing cushion 106, forehead cushion 108, frame 110 and headgear component 116 to one another is modular in nature such that any headgear component that includes a frame member 32 and a forehead frame member 138 can be used with cushion 106 and forehead cushion 108 and frame 110. Thus, a wide variety of headgear configurations, each having a frame member 32 and a forehead frame member 138, can be offered for use with cushion 106 and forehead cushion 108 and frame 110 such that a patient can choose the particular headgear component that fits their particular needs or desires ant any one time, and can change the headgear component as those needs or desires change. Also, any cushion and frame combination that has similarly positioned pegs and holes may be used with a headgear component that includes a frame member 32 and a forehead frame member 138.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
   a support frame structured to be fluidly coupled to a pressure generating device;
   a cushion structured to engage a portion of a face of a patient; and
   a headgear component structured to secure the patient interface device to a head of the patient, the headgear component having a central interface portion and at least one strap member extending from the central interface portion, the central interface portion and the at least one strap member being made of a first material that is flexible, and a frame member which defines an opening and is attached within a corresponding opening provided within the central interface portion, the frame member being made of a second material different than the first material and being removeably secured in between the cushion and the support frame and being structured to provide an airtight seal between the cushion and the support frame, the first material being a fabric material; wherein the support frame contacts the frame member.

2. The patient interface device according to claim 1, wherein the second material is a deformable material.

3. The patient interface device according to claim 2, wherein the second material is a thermoplastic material.

4. The patient interface device according to claim 1, wherein the support frame comprises a faceplate having a first opening having a first shape, wherein the cushion comprises a second opening having a second shape, wherein the frame member has a third shape and defines a third opening aligned with the first opening and the second opening, and wherein the first shape and the second shape correspond to the third shape.

5. The patient interface device according to claim 1, wherein the frame member includes a plurality of apertures that extend through the frame member, wherein the support frame includes a plurality of first connecting elements, wherein the cushion includes a plurality of second connecting elements, and wherein each first connecting element engages and removeably couples to a respective second connecting element through a respective one of the apertures.

6. The patient interface device according to claim 5, wherein each first connecting element is a peg extending from the support frame and wherein each second connecting element is a hole provided in the cushion.

7. The patient interface device according to claim 5, wherein the support frame comprises a faceplate portion and a forehead support portion, wherein the frame member is secured in between the cushion and the faceplate portion, wherein the patient interface device further includes a forehead cushion, wherein the headgear component includes a forehead portion having at least one upper strap member extending therefrom and a forehead frame member provided within the forehead portion, and wherein the forehead frame member is removeably secured in between the forehead support portion and the forehead cushion.

8. A patient interface system for selectively creating a customizable patient interface device, comprising:
a support frame structured to be fluidly coupled to a pressure generating device;
a cushion structured to engage a portion of a face of a patient; and
a plurality of headgear components, each of the headgear components having a central interface portion and a frame member which defines an opening and is attached within a corresponding opening provided within the central interface portion, the frame member of each of the headgear components being structured to be removeably secured in between the cushion and the support frame and being structured to provide an airtight seal between the cushion and the support frame, wherein each of the headgear components includes a different configuration of at least one strap member extending from the central interface portion and as such is structured to secure the support frame and the cushion to a head of the patient in a different manner, the central interface portion and the at least one strap member of each of the headgear components being made of a first material that is flexible, the frame member of each of the headgear components being made of a second material different than the first material, the first material being a fabric material; wherein the support frame contacts the frame member.

9. The patient interface system according to claim 8, wherein the frame member of each of the headgear components has the same shape and structure.

10. The patient interface system according to claim 9, wherein the support frame includes a plurality of first connecting elements, wherein the cushion includes a plurality of second connecting elements, and wherein each first connecting element is structured to engage and removeably couple to a respective second connecting element.

11. The patient interface system according to claim 10, wherein the frame member of each of the headgear components includes a plurality of apertures that extend through the frame member, wherein for each of the headgear components each first connecting element is structured to engage and removeably couple to a respective second connecting element through a respective one of the apertures.

12. The patient interface device according to claim 11, wherein each first connecting element is a peg extending from the support frame and wherein each second connecting element is a hole provided in the cushion.

13. The patient interface system according to claim 8, wherein the second material is a deformable material.

14. The patient interface system according to claim 13, wherein the second material is a thermoplastic material.

15. A patient interface device, comprising:
a support frame structured to be fluidly coupled to a pressure generating device;
a cushion structured to engage a portion of a face of a patient; and
a headgear component structured to secure the patient interface device to a head of the patient, the headgear component having a central interface portion, at least one strap member extending from the central interface portion, and a frame member provided within the central interface portion, the frame member being removeably secured in between the cushion and the support frame and being structured to provide an airtight seal between the cushion and the support frame; wherein the support frame contacts the frame member, wherein the frame member includes a plurality of apertures that extend through the frame member, wherein the support frame includes a plurality of first connecting elements, wherein the cushion includes a plurality of second connecting elements, and wherein each first connecting element engages and removeably couples to a respective second connecting element through a respective one of the apertures.

* * * * *